United States Patent
Kerman

(12) 
(10) Patent No.: US 6,214,291 B1
(45) Date of Patent: Apr. 10, 2001

(54) PAINT TEST APPARATUS

(75) Inventor: Mark Alan Kerman, Griffin, GA (US)

(73) Assignee: Markegon L.L.C., Marietta, GA (US)

( * ) Notice: Subject to any disclaimer, the term of this patent is extended or adjusted under 35 U.S.C. 154(b) by 0 days.

(21) Appl. No.: 09/158,689

(22) Filed: Sep. 22, 1998

(51) Int. Cl.[7] .................................................. G01N 31/22
(52) U.S. Cl. .............................. 422/61; 422/58; 436/164; 436/177
(58) Field of Search ................................ 422/61, 77, 58, 422/56; 436/164, 169, 177, 178

(56) References Cited

U.S. PATENT DOCUMENTS

| | | |
|---|---|---|
| 3,446,596 * | 5/1969 | Salivar et al. ................... 436/110 |
| 5,039,618 | 8/1991 | Stone . |
| 5,364,792 | 11/1994 | Stone . |
| 5,492,835 * | 2/1996 | Koenig .................... 436/77 |
| 5,550,061 | 8/1996 | Stone . |
| 5,558,835 | 9/1996 | Kozarsky et al. . |

* cited by examiner

Primary Examiner—Lyle A. Alexander
(74) Attorney, Agent, or Firm—Brooks & Kushman P.C.

(57) ABSTRACT

A test kit for determining whether paint applied to a surface is oil base paint or latex base paint. The test kit comprises a housing that has a tip at one end that retains a swab and encloses a frangible reagent container. The swab extends through the tip and is divided into two contrastingly colored portions at the end. The reagent container is initially filled with denatured alcohol and is broken to allow the alcohol to flow to the tip. The tip is then wiped across the painted surface to be tested.

11 Claims, 1 Drawing Sheet

PAINT TEST APPARATUS

TECHNICAL FIELD

The present invention relates to test kits for determining the type of paint that has been previously applied to a surface.

BACKGROUND ART

This invention is directed to the problem of determining whether the paint applied to a painted surface is an oil based paint or latex based paint. It is important to know what type of paint has been previously applied so that a compatible paint can be used to cover prior coats or so that appropriate preparations can be performed to change to a different type of paint. Paints applied to surfaces may be light colored, such as white paint, or dark colored, such as brown or green.

Professional painters test painted surfaces by applying denatured alcohol to a rag and rubbing it on the surface. If paint residue appears on the rag it is determined that the paint is a latex based paint. If no paint residue appears on the rag, it is determined that the paint is an oil based paint. While this method is effective, the denatured alcohol can be spilled and different colored rags must be used for different colored paints. For example, if the painted surface to be tested is white and the painter uses a white rag for testing it can be difficult to see whether any paint has been removed.

There is presently a need for a simple, disposable test kit that will provide clear test results regardless of the color of the paint to be tested. The test kit should not be prone to spillage but should be economical and easy to use.

The present invention, as summarized and described in detail below, provides a solution to the above noted problems that is simple, safe, economical and effective.

DISCLOSURE OF THE INVENTION

According to the present invention, a test kit for testing paint on a painted surface is provided. The test kit includes a housing having an opening at one end. A liquid test reagent is contained within the housing. A swab is disposed in the opening of the housing substantially blocking the opening. A cap is removably secured to the housing to cover the swab when placed on the housing. The cap may be removed from the housing to reveal the swab. The test kit is used by removing the cap from the housing and rubbing the swab on the painted surface to test the composition of the surface.

According to one aspect of the invention, the swab preferably has at least two contrasting colored portions that form part of a single surface of the swab. The two contrasting colored portions may be different colors but most preferably are green and white. The swab may be formed in two separate portions or may be formed of a single portion that is dyed or colored at the end surface.

According to another aspect of the invention, the liquid test reagent is denatured alcohol. The denatured alcohol is preferably retained in a breakable glass vial until the test kit is ready to be used.

According to another aspect of the invention, the housing and cap are generally cylindrical in shape. The swab may also be a cylindrical member having a first semi-cylindrical portion formed of one color felt material and a second semi-cylindrical portion formed of a second contrasting color of felt.

These and other advantages and features of the invention will be better understood in view of the attached drawings and the following detailed description of a preferred embodiment of the paint test kit of the present invention.

BEST MODE FOR CARRYING OUT THE INVENTION

Figure 1:
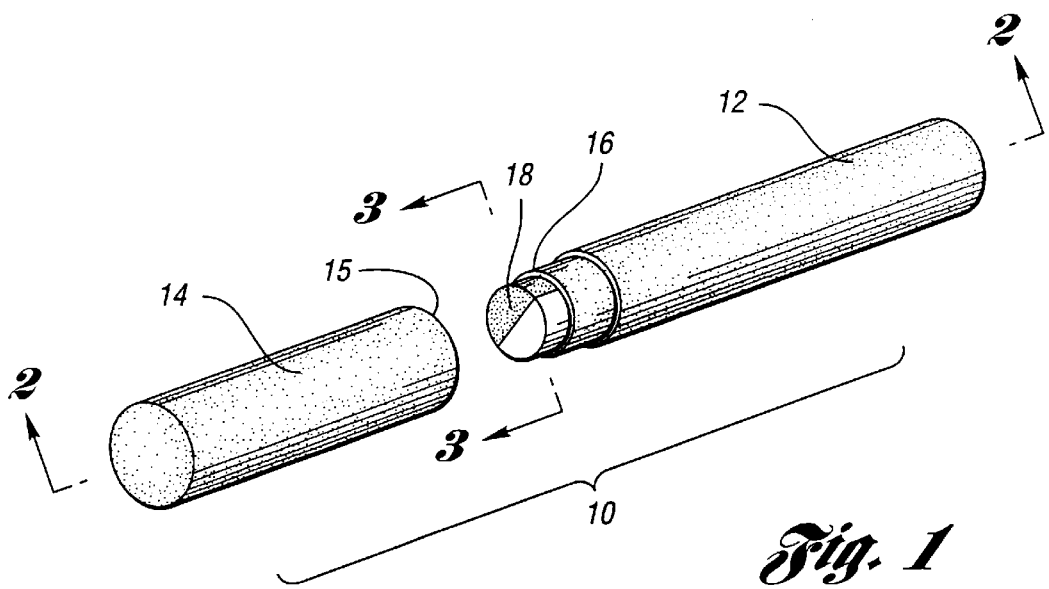
FIG. 1 is a perspective view of the paint test kit of the present invention.
Figure 2:
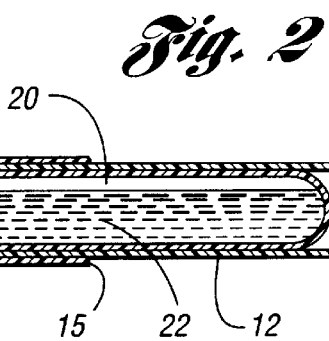
FIG. 2 is a cross-sectional view taken a long the line 2—2 in FIG. 1.
Figure 3:
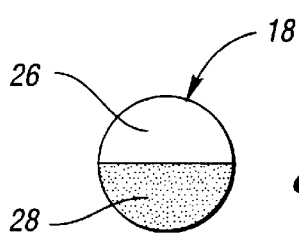
FIG. 3 is a cross-sectional view taken along the line 3—3 in FIG. 1.
Figure 4:
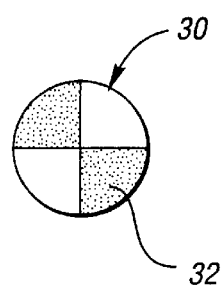
FIG. 4 is a end view of an alternative embodiment of a swab used in the present invention.

Referring now to FIGS. 1 and 2, a test kit 10 is illustrated. The test kit 10 includes a housing 12 formed of a rigid, flexible, plastic material that is cylindrical in shape and a cap 14 has an opening 15 formed at one end. A swab 18 formed of a relatively rigid absorbent felt material that is received in an opening 16 in the housing 12 in a substantially sealing relationship so that it blocks the opening 16. A frangible, or breakable, glass vial 20 shown in FIG. 2 is retained in the housing 12. The vial 20 holds a test reagent 22, such a denatured alcohol, until a force is applied to the housing 12 that causes the vial 20 to break. When the vial 20 breaks, the housing 12 is held with its opening 16 in a downwardly orientation so that the test reagent 22 will flow to the swab 18 wetting the swab 18 with the test reagent 22.

A cap 14 is preferably provided to keep the swab 18 clean until the test kit is ready to be used. The cap is also provided to inhibit spilling of the test reagent 22 from the housing 10 through the opening 16 when the vial 20 is broken. The cap 14 is preferably formed of a cardboard material in a generally cylindrical shape.

The swab 18 is preferably formed of a relatively hard, or stiff, felt material that is absorbent to allow the test reagent to be absorbed and retained in the swab 18. The felt material is preferably formed in two separate portions 26 and 28 each being a contrasting color. The felt material may be formed as two semi-cylindrical felt swabs for maximum contrast. White felt provides the best contrast for colored paints while green felt is suitable for testing white painted surfaces.

Alternatively, a swab 30 could be formed in a single piece and be provided with a ink or dye 32 that would provide contrasting portions on an end surface of the swab.

Figure 5:
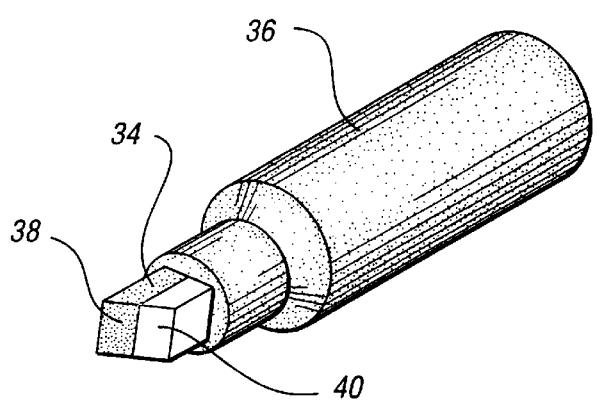
FIG. 5 is a perspective view of an alternative embodiment of the present invention.

Referring now to FIG. 5, an alternative embodiment of the present invention is shown wherein the test kit will be formed of a pre-impregnated felt swab 34 that is substantially contained within a housing 36 formed of an impermeable plastic material that is not adversely affected by the denatured alcohol contained on the swab 34. The test kit would also include a cap such as cap 14 shown in the embodiment of FIG. 1 that would be received on the end of the housing 36 in a sealing relationship. In the embodiment of FIG. 5, it is not necessary to break a frangible vial to release the test reagent and the test kit may be simply used by removing the cap and wiping the end of the swab 34 on the surface to be tested. The swab 34 is preferably formed in two parts with a dark felt section 38 and a white felt portion 40.

The preceding description is of the best mode of the invention. It will be readily appreciated by one of ordinary skill in the art that the present invention may be modified and various alternatives may be utilized in practicing the present invention.

What is claimed is:

1. A test kit for testing the presence of latex paint on a painted surface comprising:

a housing having an opening at one end;

a latex paint solvent contained within the housing;

an absorbent swab disposed in the opening of the housing, substantially blocking the opening, the swab having at least two contrasting colored portions that form part of a single surface of the swab; and a cap removably secured to the housing covering the swab when placed on the housing and revealing the swab when removed from the housing, after said solvent is absorbed onto the swab, said cap being removed from the housing so that the swab may be rubbed on the painted surface to test the composition of the paint on the surface wherein the presence of latex paint is indicated by a change of color of the colored portions.

2. The test kit of claim 1 wherein the swab has at least two contrasting colored portions that form part of a single surface of the swab.

3. The test kit of claim 1 wherein at least two contrasting colored portions are independently formed of different colored felt.

4. The test kit of claim 1 wherein at least two contrasting colored portions are green and white.

5. The test kit of claim 1 wherein the solvent is denatured alcohol.

6. The test kit of claim 1 wherein the solvent is contained in a vial formed of a frangible material.

7. The test kit of claim 6 wherein the vial is formed of glass.

8. The test kit of claim 1 wherein the cap is formed of plastic and forms a hermetic seal over the swab when placed on the end of the housing.

9. The test kit of claim 1 wherein the housing and cap are generally cylindrical in shape and the swab is a cylindrical member having a first semi-cylindrical portion formed of one color of felt and a second semi-cylindrical portion formed of a second contrasting color of felt wherein said second color contrasts with said one color of felt forming the first semi-cylindrical portion.

10. The test kit for testing the presence of latex paint on a painted surface comprising:

a generally cylindrical housing having an opening at one end;

a frangible vial disposed within the housing, said vial containing a latex paint solvent;

a swab disposed in and substantially blocking the opening of the housing, said swab being a cylindrical member having a first semi-cylindrical portion formed of one color of felt and a second semi-cylindrical portion formed of a second contrasting color of felt wherein said second color contrasts with said one color of felt forming the first semi-cylindrical portion; and a cap removably secured to the housing to cover the swab when placed on the housing and revealing the swab when removed from the housing after said vial is broken to dispense the solvent onto the swab, said cap is removed from the housing so that the swab may be rubbed on the painted surface to test the composition of the surface wherein the presence of latex paint is indicated by a change of color of the colored portion.

11. The test kit of claim 10 wherein the cap is formed of cardboard.

* * * * *